United States Patent
Miyazaki et al.

(10) Patent No.: US 12,384,970 B2
(45) Date of Patent: *Aug. 12, 2025

(54) SURFACTANT COMPOSITION

(71) Applicant: KAO CORPORATION, Tokyo (JP)

(72) Inventors: Atsushi Miyazaki, Wakayama (JP); Haruna Ichihashi, Wakayama (JP)

(73) Assignee: KAO CORPORATION, Tokyo (JP)

(*) Notice: Subject to any disclaimer, the term of this patent is extended or adjusted under 35 U.S.C. 154(b) by 492 days.

This patent is subject to a terminal disclaimer.

(21) Appl. No.: 17/422,492

(22) PCT Filed: Feb. 13, 2020

(86) PCT No.: PCT/JP2020/005437
§ 371 (c)(1),
(2) Date: Jul. 13, 2021

(87) PCT Pub. No.: WO2020/166640
PCT Pub. Date: Aug. 20, 2020

(65) Prior Publication Data
US 2022/0072490 A1    Mar. 10, 2022

(30) Foreign Application Priority Data

Feb. 13, 2019   (JP) ................ 2019-023710

(51) Int. Cl.
| | | |
|---|---|---|
| C09K 23/00 | (2022.01) |
| A61K 8/41 | (2006.01) |
| A61K 8/46 | (2006.01) |
| A61Q 5/12 | (2006.01) |
| A61Q 19/10 | (2006.01) |
| C09K 23/02 | (2022.01) |
| C09K 23/18 | (2022.01) |
| D06M 13/188 | (2006.01) |
| D06M 13/256 | (2006.01) |
| D06M 13/463 | (2006.01) |
| D06M 101/06 | (2006.01) |

(52) U.S. Cl.
CPC ............ *C09K 23/017* (2022.01); *A61K 8/416* (2013.01); *A61K 8/466* (2013.01); *A61Q 5/12* (2013.01); *A61Q 19/10* (2013.01); *C09K 23/00* (2022.01); *C09K 23/02* (2022.01); *C09K 23/18* (2022.01); *D06M 13/188* (2013.01); *D06M 13/256* (2013.01); *D06M 13/463* (2013.01); *D06M 2101/06* (2013.01)

(58) Field of Classification Search
None
See application file for complete search history.

(56) References Cited

U.S. PATENT DOCUMENTS

| | | | |
|---|---|---|---|
| 3,404,991 A | 10/1968 | Pelham et al. | |
| 5,051,251 A * | 9/1991 | Morita ............... | A61K 8/416 424/70.28 |
| 5,573,709 A | 11/1996 | Wells | |
| 5,863,909 A | 1/1999 | Kurita et al. | |
| 6,008,181 A | 12/1999 | Cripe et al. | |
| 8,283,306 B2 | 10/2012 | Guyot et al. | |
| 2003/0147822 A1 | 8/2003 | Doi et al. | |
| 2007/0269397 A1 | 11/2007 | Terada | |
| 2013/0005835 A1 | 1/2013 | Uyama et al. | |
| 2014/0080751 A1 * | 3/2014 | Yoshikawa ........... | A61Q 19/10 510/498 |
| 2019/0169536 A1 | 6/2019 | Tabuchi et al. | |
| 2020/0155435 A1 | 5/2020 | Tetsu et al. | |
| 2020/0368130 A1 | 11/2020 | Tetsu et al. | |

FOREIGN PATENT DOCUMENTS

| | | |
|---|---|---|
| CN | 1062837 A | 7/1992 |
| CN | 1137887 A | 12/1996 |
| CN | 1173110 A | 2/1998 |
| CN | 1222186 A | 7/1999 |
| CN | 1627933 A | 6/2005 |

(Continued)

OTHER PUBLICATIONS

International Search Report issued Apr. 7, 2020 in PCT/JP2020/005437 (with English translation), 5 pages.

(Continued)

*Primary Examiner* — Jennifer A Berrios
(74) *Attorney, Agent, or Firm* — Element IP, PLC

(57) ABSTRACT

The present invention relates to a surfactant composition capable of making a liquid oil highly remain on the solid surface, which is a surfactant composition containing an anionic surfactant (A), a cationic surfactant (B), a liquid oil (C), and water, wherein the water constitutes a continuous phase; the following molar ratio $R_A$ is 0.25 or more and 0.60 or less; and the following molar ratio $R_b$ is 0.6 or more:

$R_A$: a molar ratio $\{(A)/[(A)+(B)]\}$ of the amount of the anionic surfactant (A) to the total amount of the anionic surfactant (A) and the cationic surfactant (B)

$R_b$: a molar ratio $\{[(a1)+(b1)]/[(A)+(B)]\}$ of the total amount of a branched-type anionic surfactant (a1) and a branched-type cationic surfactant (b1) to the total amount of the anionic surfactant (A) and the cationic surfactant (B).

12 Claims, No Drawings

(56) References Cited

FOREIGN PATENT DOCUMENTS

| | | | |
|---|---|---|---|
| CN | 101077331 | A | 11/2007 |
| CN | 108251228 | A | 7/2018 |
| EP | 0729742 | A2 | 9/1996 |
| ES | 306758 | A1 | 5/1965 |
| JP | H09-52820 | A | 2/1997 |
| JP | 2001181133 | A | 7/2001 |
| JP | 2002060787 | A | 2/2002 |
| JP | 2005112756 | A | 4/2005 |
| JP | 2008001685 | A | 1/2008 |
| JP | 2010090278 | A | 4/2010 |
| JP | 2010168336 | A | 8/2010 |
| JP | 2011521083 | A | 7/2011 |
| JP | 2011213702 | A | 10/2011 |
| JP | 2012107104 | A | 6/2012 |
| JP | 2014076983 | A | 5/2014 |
| JP | 2015027974 | A | 2/2015 |
| JP | 2015027977 | A | 2/2015 |
| JP | 2019034927 | A | 3/2019 |
| JP | 2019034928 | A | 3/2019 |
| TW | 201831665 | A | 9/2018 |
| WO | WO-2009035970 | A1 | 3/2009 |
| WO | WO-2020166639 | A1 | 8/2020 |

OTHER PUBLICATIONS

Extended European Search Report issued Sep. 8, 2022 in Patent Application No. 20755933.7, 10 pages.
U.S. Appl. No. 16/636,934, filed Feb. 6, 2020, Makio Tetsu.
U.S. Appl. No. 16/636,675, filed Feb. 5, 2020, Makio Tetsu.

\* cited by examiner

SURFACTANT COMPOSITION

FIELD OF THE INVENTION

The present invention relates to a surfactant composition.

BACKGROUND OF THE INVENTION

There are various solid surfaces, such as glasses, metals, plastics, clothes, skins, and hairs, in personal belongings. The feel, lubricity, wettability, chargeability, and the like of the solid surface are determined by properties of the solid surface, and a surfactant or a liquid oil is generally used for controlling them. In particular, to make the liquid oil remain on the solid surface is a method with extremely high effectiveness because the properties of the solid surface, such as wettability, can be greatly changed.

With respect to cleansing agents and conditioning agents containing a surfactant or a liquid oil, there have hitherto been made various proposals.

For example, JP 2010-90278 A (PTL 1) discloses a liquid cleansing composition for clothing containing specified first and second nonionic surfactants, an anionic surfactant having an $SO_3$ group or an $SO_4$ group, a specified quaternary ammonium compound, and a water-insoluble silicone compound.

JP 2012-107104 A (PTL 2) discloses a cleansing composition in the hair/skin cleansing field containing specified amounts of an anionic surfactant, a cationic surfactant, a dimethylpolysiloxane having a kinematic viscosity at 25° C. of 4,000,000 mm$^2$/s or more, and maltooligosaccharide.

JP 2015-27977 A (PTL 3) discloses a cleansing composition for skin or hair containing an internal olefin sulfonate having 12 to 24 carbon atoms.

JP 2015-27974 A (PTL 4) discloses a cleansing composition for skin or hair containing an internal olefin sulfonate having 12 to 24 carbon atoms and an oil solution.

SUMMARY OF THE INVENTION

The present invention relates to a surfactant composition containing an anionic surfactant (A), a cationic surfactant (B), a liquid oil (C), and water, wherein
  the water constitutes a continuous phase;
  the following molar ratio $R_A$ is 0.25 or more and 0.60 or less; and
  the following molar ratio $R_b$ is 0.6 or more:
  $R_A$: a molar ratio $\{(A)/[(A)+(B)]\}$ of the amount of the anionic surfactant (A) to the total amount of the anionic surfactant (A) and the cationic surfactant (B)
  $R_b$: a molar ratio $\{[(a1)+(b1)]/[(A)+(B)]\}$ of the total amount of a branched-type anionic surfactant (a1) and a branched-type cationic surfactant (b1) to the total amount of the anionic surfactant (A) and the cationic surfactant (B).

DETAILED DESCRIPTION OF THE INVENTION

In order to greatly change the properties of the solid surface, it is desired to make a liquid oil highly remain on the solid surface. However, according to the conventional surfactant composition-containing cleansing agents as in PTLs 1 to 4, it is difficult to make a liquid oil highly remain on the solid surface.

The present invention relates to a surfactant composition capable of making a liquid oil highly remain on the solid surface.

The present inventors have found that the aforementioned problem can be solved by a surfactant composition containing an anionic surfactant, a cationic surfactant, a liquid oil, and water, in which a branched-type anionic surfactant and a branched-type cationic surfactant are blended in a specified proportion.

Specifically, the present invention relates to a surfactant composition containing an anionic surfactant (A), a cationic surfactant (B), a liquid oil (C), and water, wherein
  the water constitutes a continuous phase;
  the following molar ratio $R_A$ is 0.25 or more and 0.60 or less; and
  the following molar ratio $R_b$ is 0.6 or more:
  $R_A$: a molar ratio $\{(A)/[(A)+(B)]\}$ of the amount of the anionic surfactant (A) to the total amount of the anionic surfactant (A) and the cationic surfactant (B)
  $R_b$: a molar ratio $\{[(a1)+(b1)]/[(A)+(B)]\}$ of the total amount of a branched-type anionic surfactant (a1) and a branched-type cationic surfactant (b1) to the total amount of the anionic surfactant (A) and the cationic surfactant (B).

In accordance with the present invention, it is possible to provide a surfactant composition capable of making a liquid oil highly remain on the solid surface.

[Surfactant Composition]

The surfactant composition of the present invention is a surfactant composition containing an anionic surfactant (A), a cationic surfactant (B), a liquid oil (C), and water, wherein
  the water constitutes a continuous phase;
  the following molar ratio $R_A$ is 0.25 or more and 0.60 or less; and
  the following molar ratio $R_b$ is 0.6 or more:
  $R_A$: a molar ratio $\{(A)/[(A)+(B)]\}$ of the amount of the anionic surfactant (A) to the total amount of the anionic surfactant (A) and the cationic surfactant (B)
  $R_b$: a molar ratio $\{[(a1)+(b1)]/[(A)+(B)]\}$ of the total amount of a branched-type anionic surfactant (a1) and a branched-type cationic surfactant (b1) to the total amount of the anionic surfactant (A) and the cationic surfactant (B).

In the surfactant composition of the present invention, either one or both of the anionic surfactant (A) (hereinafter also referred to as "component (A)") and the cationic surfactant (B) (hereinafter also referred to as "component (B)") are surfactant of a branched type. That is, the surfactant composition of the present invention contains either one of the branched-type anionic surfactant (a1) (hereinafter also referred to as "component (a1)") and the branched-type cationic surfactant (b1) (hereinafter also referred to as "component (b1)") and preferably contains both the component (a1) and the component (b1).

The term "branched type" as referred to herein means that in the surfactant having a hydrophobic group and a hydrophilic group, the hydrophobic group has at least one branched structure, or the surfactant has a plurality of linear or branched hydrophobic groups are existent. Examples of the hydrophobic group of the branched-type surfactant include a hydrocarbon group having a linear or branched structure, and more preferably an alkyl group or an aryl group each having a linear or branched structure which may contain a substituent or a connecting group.

In the present invention, the molar ratio $R_b$ $\{[(a1)+(b1)]/[(A)+(B)]\}$ of the total amount of the component (a1) and the component (b1) to the total amount of the component (A) and the component (B) is 0.6 or more.

From the viewpoint of emulsion stability of the liquid oil (C) (hereinafter also referred to as "component (C)") in the composition and making the component (C) highly remain on the solid surface, the molar ratio $R_b$ is preferably 0.7 or more, more preferably 0.8 or more, and still more preferably 0.9 or more, and it is preferably 1.0 or less.

The amount of the component (a1) can be determined by combining titration with a cationic surfactant and analysis, such as NMR and LC-MS, or comparing with an authentic sample having the same structure. In addition, the amount of the component (b1) can be determined by combining titration with an anionic surfactant and analysis, such as NMR and LC-MS, or comparing with an authentic sample having the same structure.

By applying the surfactant composition of the present invention onto the solid surface, the liquid oil (C) can be made to highly remain. In other words, the surfactant composition of the present invention is used in order to make the liquid oil (C) highly remain on the solid surface.

Although the reason why the liquid oil (C) can be made to highly remain is not elucidated yet, it may be considered that the surfactant composition of the present invention is able to emulsify the liquid oil (C) in water, and emulsion droplets of the liquid oil are apt to attach onto the solid surface.

In addition, it may be considered that by containing the component (a1) and the component (b1) in specified proportions, the remaining properties of the liquid oil (C) on the solid surface can be effectively improved.

Although the form of the surfactant composition of the present invention is not particularly restricted, from the viewpoint of handling properties, an aqueous system is preferred, and an aqueous solution containing the surfactant composition of the present invention, in which water is a continuous phase, is preferred.

<Anionic Surfactant: Component (A)>

Although the component (A) which is contained in the surfactant composition of the present invention is not particularly restricted, it is preferred to contain at least one selected from a sulfonic acid salt type surfactant and a sulfuric acid ester salt type surfactant.

[Sulfonic Acid Salt Type Surfactant]

Examples of the sulfonic acid salt type surfactant include surfactants of a sulfonic acid salt type having an aliphatic hydrocarbon group having 6 or more and 22 or less carbon atoms. Suitable examples thereof include an alkylbenzenesulfonic acid salt, an alkylsulfosuccinic acid salt, and an alkylsulfonic acid salt, each having an alkyl group having 6 or more and 22 or less carbon atoms. In the case of the alkylbenzenesulfonic acid salt, the alkyl group having 6 or more and 22 or less carbon atoms means an alkyl group substituting on the benzene ring and does not include the benzene skeleton. From the viewpoint of high remaining properties of the component (C) on the solid surface, the carbon number of the alkyl group is preferably 8 or more, more preferably 10 or more, and still more preferably 12 or more, and it is preferably 20 or less, and more preferably 18 or less.

Examples of the aforementioned salt include an alkali metal salt of sodium, potassium, etc., an alkanolamine salt, and an alkaline earth metal salt of magnesium, calcium, etc. Among those, an alkali metal salt is preferred, and a sodium salt is more preferred from the same viewpoint as mentioned above.

[Sulfuric Acid Ester Salt Type Surfactant]

Examples of the sulfuric acid ester salt type surfactant include surfactants of a sulfuric acid ester salt type having an aliphatic hydrocarbon group having 10 or more and 18 or less carbon atoms. Suitable examples of the sulfuric acid ester salt include a polyoxyalkylene alkyl ether sulfuric acid ester salt.

Specific examples thereof include those in which not only an average addition molar number m of the alkyleneoxy group is 0, preferably 0.5 or more, and more preferably 1 or more, and it is 5 or less, preferably 4 or less, and more preferably 3 or less, but also the carbon number of the alkyl group is 10 or more, and preferably 12 or more, and it is 18 or less, and preferably 16 or less.

The alkyleneoxy group preferably contains an ethyleneoxy group (EO group) and may contain a PO group within a range of 0.2 to 2 mols in terms of an average addition molar number.

Examples of the aforementioned salt include an alkali metal salt of sodium, potassium, etc., an alkanolamine salt, and an alkaline earth metal salt of magnesium, calcium, etc. Among those, an alkali metal salt is preferred, and a sodium salt is more preferred from the same viewpoint as mentioned above.

The surfactant composition of the present invention contains the branched-type anionic surfactant (a1).

As the component (a1), one represented by the following general formula (1) is preferred.

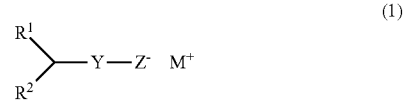

(1)

In the formula (1), $R^1$ and $R^2$ each independently represent a hydrocarbon group which may contain a substituent or a connecting group; the total carbon number of $R^1$ and $R^2$ is 5 or more and 29 or less; Y represents a single bond or a phenylene group; Z represents a group selected from a —$SO_3$ group and a —$OSO_3$ group; and M represents a cation.

From the same viewpoint as mentioned above, in the formula (1), the carbon numbers of $R^1$ and $R^2$ are each independently 1 or more, preferably 2 or more, more preferably 3 or more, and still more preferably 4 or more, and they are preferably 28 or less, more preferably 26 or less, and still more preferably 24 or less.

The hydrocarbon group represented by $R^1$ and $R^2$ is preferably an aliphatic hydrocarbon group, and more preferably an alkyl group, an alkenyl group, or a hydroxyalkyl group.

From the same viewpoint as mentioned above, the total carbon number of $R^1$ and $R^2$ is preferably 7 or more, more preferably 9 or more, and still more preferably 11 or more, and it is preferably 23 or less, more preferably 19 or less, and still more preferably 17 or less.

The hydrocarbon group represented by $R^1$ and $R^2$ may contain a substituent, such as a hydroxy group, or a connecting group, such as a COO group. The carbon number of the aforementioned substituent or connecting group is not calculated into the carbon number of the hydrocarbon group represented by $R^1$ and $R^2$.

Y is a single bond or a phenylene group, with a single bond being preferred.

Examples of the cation M in the formula (1) include an alkali metal ion and an alkanolammonium ion having 1 or more and 6 or less carbon atoms. Among those, at least one selected from a sodium ion, a potassium ion, a monoethanolammonium ion, a diethanolammonium ion, and a triethanolammonium ion is preferred.

From the viewpoint of emulsion stability of the component (C) and high remaining properties onto the solid surface, the component (a1) is preferably at least one selected d from an internal olefin sulfonate (IOS), an alkylbenzenesulfonate, a secondary alkanesulfonate, and a dialkylsulfosuccinate, with IOS being more preferred.

(Internal Olefin Sulfonate: IOS)

The IOS can be obtained by sulfonating an internal olefin in which a double bond is existent in the interior of an olefin chain (at the 2-position or higher position), followed by neutralization and then hydrolysis. When the internal olefin is sulfonated, β-sultone is quantitatively produced, and a part of the β-sultone is converted into γ-sultone and an olefin sulfonic acid, which are further converted into a hydroxyalkane sulfonate (H-body) and an olefin sulfonate (O-body) in the neutralization/hydrolysis process (see, for example, "J. Am. Oil Chem. Soc., 69, 39 (1992)"). The IOS is a mixture of these materials and is mainly a sulfonate in which a sulfonate group is existent in the interior (at the 2-position or higher position) of a carbon chain (a hydroxyalkane chain in the H-body or an olefin chain in the O-body).

From the same viewpoint as mentioned above, the carbon number of the IOS is preferably 14 or more, and more preferably 16 or more, and it is preferably 20 or less, and more preferably 18 or less. The aforementioned carbon number is the carbon number as expressed in terms of an acid-type compound.

Examples of the salt of IOS include an alkali metal salt, an alkaline earth metal (½ atom) salt, an ammonium salt, and an organic ammonium salt. Examples of the alkali metal salt include a sodium salt and a potassium salt. Examples of the alkaline earth metal salt include a calcium salt and a magnesium salt. Examples of the organic ammonium salt include an alkanolammonium salt having 2 or more and 6 or less carbon atoms.

In the IOS, from the same viewpoint as mentioned above, a mass ratio of the content of an internal olefin sulfonate having 16 carbon atoms (hereinafter also referred to as "(16S) component") to the content of an internal olefin sulfonate having 18 carbon atoms (hereinafter also referred to as "(18S) component" [(16S) component/(18S) component] is preferably 50/50 to 99/1, more preferably 60/40 to 95/5, still more preferably 70/30 to 90/10, and yet still more preferably 75/25 to 85/15.

In the IOS, from the same viewpoint as mentioned above, the total content of the (16S) component and the (18S) component is preferably 50% by mass or more, more preferably 70% by mass or more, still more preferably 90% by mass or more, and yet still more preferably 100% by mass.

In the IOS, from the same viewpoint as mentioned above, the content of the internal olefin sulfonate in which the sulfonate group is existent at the 2-position is preferably 5% by mass or more, more preferably 7% by mass or more, and still more preferably 10% by mass or more, and it is preferably 35% by mass or less, more preferably 30% by mass or less, and still more preferably 28% by mass or less.

In the IOS, the mass ratio of H-body/O-body, the substitution position distribution of the sulfonate group, and so on can be measured by high performance liquid chromatography/mass spectrometry (HPLC-MS), gas chromatography, nuclear magnetic resonance spectrometry, or the like. More specifically, the measurement can be performed by the methods described in JP 2015-27977 A and JP 2018-66102 A.

Details of the internal olefin sulfonate and a method for producing the same can be made by reference to JP 2015-27977 A, Japanese Patent No. 1633184, Japanese Patent No. 2625150, "Tenside Surf. Det., 31 (5) 299 (1994)", and so on.

<Cationic Surfactant: Component (B)>

From the viewpoint of emulsion stability of the component (C) and high remaining properties onto the solid surface, the surfactant composition of the present invention contains the cationic surfactant (B).

It is preferred that the component (B) contains the branched-type cationic surfactant (b1).

From the same viewpoint as mentioned above, the component (B) preferably contains a quaternary ammonium salt type cationic surfactant, and more preferably contains at least one selected those represented by any of the following general formulae (2) and (3). From the same viewpoint as mentioned above, the component (b1) is more preferably at least one selected from those represented by any of the following general formulae (2) and (3).

As for the quaternary ammonium salt represented by any of the general formulae (2) and (3), one or a combination of two or more specific compounds included in any of the formulae (2) and (3) can be used. The foregoing component is typically used as a mixture containing plural compounds.

[Quaternary Ammonium Salt Represented by General Formula (2)]

(2)

In the formula, $R^3$ and $R^4$ each independently represent a hydrocarbon group having 6 or more and 26 or less carbon atoms; $R^5$ and $R^6$ each independently represent an alkyl group having 1 or more and 3 or less carbon atoms; and $X^-$ represents an anion.

The hydrocarbon group represented by $R^3$ is preferably an aliphatic hydrocarbon group, and more preferably an alkyl group.

The hydrocarbon group represented by $R^4$ is preferably an aliphatic hydrocarbon group or an aryl group, and more preferably an alkyl group or a benzyl group.

From the same viewpoint as mentioned above, the carbon number of the aliphatic hydrocarbon group represented by $R^3$ and $R^4$ is preferably 8 or more, more preferably 10 or more, and still more preferably 12 or more, and it is preferably 22 or less, and more preferably 20 or less. From the same viewpoint as mentioned above, the aliphatic hydrocarbon group is preferably an alkyl group. Specific examples thereof include various octyl groups, various decyl groups, various dodecyl group, various tetradecyl groups, various hexadecyl groups, various octadecyl groups, and various eicosyl groups.

From the same viewpoint as mentioned above, the aryl group represented by $R^4$ is preferably a benzyl group.

From the viewpoint of easiness of availability and the same viewpoint as mentioned above, the alkyl group having 1 or more and 3 or less carbon atoms represented by $R^5$ and $R^6$ is a methyl group, an ethyl group, a propyl group, or an isopropyl group, preferably a methyl group or an ethyl group, and more preferably a methyl group.

In the formula (2), examples of the anion represented by $X^-$ include organic or inorganic anions. Specific examples of the anion $X^-$ include a halogen ion, an alkyl sulfate ion having 1 or more and 3 or less carbon atoms, an alkyl phosphate ion having 1 or more and 3 or less carbon atoms, a fatty acid ion having 12 or more and 18 or less carbon atoms, and a benzenesulfonic acid ion on which one or more and three or less alkyl groups having 1 or more and 3 or less carbon atoms may be substituted. Among these, a halogen ion or an alkyl sulfate ion having 1 or more and 3 or less carbon atoms is preferred; a chlorine ion, a bromine ion, a methyl sulfate ion, or an ethyl sulfate ion is more preferred; and a chlorine ion or a methyl sulfate ion is still more preferred.

Suitable examples of the quaternary ammonium salt represented by the formula (2) include a didecyl (C10) dimethylammonium salt, a dilauryl (C12) dimethylammonium salt, a dicoco dimethylammonium salt (C8 to 16), a dimyristyl (C14) dimethylammonium salt, a dicetyl (C16) dimethylammonium salt, a distearyl (C18) dimethylammonium salt, a diarachidoyl (C20) dimethylammonium salt, a dibiphenyl (C22) dimethylammonium salt, a stearyl lauryl dimethylammonium salt, a dialkyl(C12 to 15) dimethylammonium salt, and a dialkyl(C12 to 18) dimethylammonium salt. Among these, from the same viewpoint as mentioned above, a dialkyl(C12 to 15) dimethylammonium salt, a dicetyl (C16) dimethylammonium salt, and a dialkyl(C12 to 18) dimethylammonium salt are preferred, and chlorides thereof are more preferred.

Examples of commercially available products of the quaternary ammonium salt represented by the formula (2) include "QUARTAMIN" Series, manufactured by Kao Corporation; VARISOFT 432PPG (dicetyldimonium chloride), manufactured by Evonik Nutrition & Care GmbH; RQUAD PC 2C-75 (dicocodimonium chloride), manufactured by Akzo Nobel N.V.; and LIPOQUAD 2C-75 (dicoconut alkyl dimethylammonium chloride), manufactured by Lion Specialty Chemicals Co., Ltd.

[Quaternary Ammonium Salt Represented by General Formula (3)]

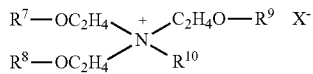

(3)

In the formula, $R^7$, $R^8$, and $R^9$ each independently represent an acyl group having 8 or more and 22 or less carbon atoms or a hydrogen atom, provided that $R^7$, $R^8$, and $R^9$ are not a hydrogen atom at the same time; $R^{10}$ represents an alkyl group having 1 or more and 3 or less carbon atoms; and X represents an anion.

The quaternary ammonium salt represented by the general formula (3) preferably includes a compound in which two of $R^7$, $R^8$, and $R^9$ in the formula (3) are an acyl group. Specifically, it is preferred to contain at least one selected from a compound represented by the formula (3) in which $R^7$ is an acyl group, and $R^8$ and $R^9$ are a hydrogen atom; a compound represented by the formula (3) in which $R^7$ and $R^8$ are an acyl group, and $R^9$ is a hydrogen atom; and a compound represented by the formula (3) in which $R^7$, $R^8$, and $R^9$ are an acyl group.

From the viewpoint of emulsion stability of the component (C) and high remaining properties onto the solid surface, the carbon number of the acyl group represented by $R^7$ to $R^9$ is preferably 10 or more, more preferably 14 or more, and still more preferably 16 or more, and it is preferably 20 or less, and more preferably 18 or less.

From the same viewpoint as mentioned above, specific examples of $R^7$ to $R^9$ include preferably an aliphatic acyl group, more preferably a linear aliphatic acyl group, and still more preferably a linear alkanoyl group or a linear alkenoyl group. Examples of the linear alkanoyl group include a hexadecanoyl group and an octadecanoyl group. Examples of the linear alkenoyl group include an oleoyl group.

The acyl group is represented by $R^{11}$—CO— (in the formula, $R^{11}$ represents a hydrocarbon group); the aliphatic acyl group is one in which $R^{11}$ is an aliphatic hydrocarbon group; the linear aliphatic acyl group is one in which $R^{11}$ is a linear aliphatic hydrocarbon group; the linear alkanoyl group is one in which $R^{11}$ is a linear alkyl group; and the linear alkenoyl group is one in which $R^{11}$ is a linear alkenyl group. The carbon number of the acyl group is a number resulting from adding 1 to the carbon number of $R^{11}$.

From the same viewpoint as mentioned above, $R^{10}$ in the formula (3) is preferably a methyl group or an ethyl group, and more preferably a methyl group.

In the formula (3), examples of the anion represented by $X^-$ include an organic or inorganic anion. Specific examples of the anion $X^-$ include a halogen ion, an alkyl sulfate ion having 1 or more and 3 or less carbon atoms, an alkyl phosphate ion having 1 or more and 3 or less carbon atoms, a fatty acid ion having 12 or more and 18 or less carbon atoms, and a benzenesulfonic acid ion on which one or more and three or less alkyl groups having 1 or more and 3 or less carbon atoms may be substituted. Among these, a halogen ion or an alkyl sulfate ion having 1 or more and 3 or less carbon atoms is preferred; a chlorine ion, a bromine ion, a methyl sulfate ion, or an ethyl sulfate ion is more preferred; and a chlorine ion or a methyl sulfate ion is still more preferred.

<Liquid Oil (C)>

The liquid oil (C) which is used in the present invention is one which is in a liquid form at a temperature at the time of use (0° C. to 100° C.). The liquid oil (C) is not particularly restricted so long as it is sparingly water-soluble or water-insoluble, and its solubility in 100 g of water at 20° C. is preferably 1 g or less. In addition, from the viewpoint of making it easy to uniformly spread onto the solid surface, one which is in a liquid form at room temperature (0° C. to 45° C.) is preferred, and one which is in a liquid form at 25° C. is more preferred.

Suitable examples of the liquid oil (C) include at least one selected from an ester oil, an ether oil, an aliphatic higher alcohol, a hydrocarbon oil, and a silicone oil.

Examples of the ester oil include isopropyl myristate, octyl myristate, isopropyl palmitate, octyl palmitate, stearyl palmitate, isopropyl stearate, octyl stearate, stearyl stearate, and isopropyl isostearate.

Examples of the ether oil include dihexyl ether, dioctyl ether, didecyl ether, dilauryl ether, dimyristyl ether, dicetyl ether, distearyl ether, dieicosyl ether, and dibiphenyl ether.

Examples of the aliphatic higher alcohol include alcohols having a linear or branched alkyl group or alkenyl group having 8 or more and 26 or less carbon atoms, preferably 12 or more and 22 or less carbon atoms, and more preferably 16 or more and 20 or less carbon atoms. More specifically, examples thereof include myristyl alcohol, cetyl alcohol, stearyl alcohol, arachidyl alcohol, behenyl alcohol, isostearyl alcohol, 2-octyl dodecanol, oleyl alcohol, and mixtures thereof.

Examples of the hydrocarbon oil include an a olefin oligomer, a liquid isoparaffin, a liquid paraffin, and squalane.

Examples of the silicone oil include chained polysiloxanes, such as dimethylpolysiloxane, methylphenylpolysiloxane, methylhydrogenpolysiloxane, and dimethiconol; and modified silicones, such as a polyether-modified silicone, a polyamino-modified silicone, an alcohol-modified silicone, a fluorine-modified silicone, and a fatty acid-modified silicone.

The dimethylpolysiloxane is preferably a linear dimethylpolysiloxane, and its kinematic viscosity at 25° C. is preferably 2 mm$^2$/s or more, more preferably 4 mm$^2$/s or more, and still more preferably 10 mm$^2$/s or more, and it is preferably 100 mm$^2$/s or less, more preferably 80 mm$^2$/s or less, and still more preferably 60 mm$^2$/s or less.

The kinematic viscosity is measured by the method described in the section of Examples.

Other examples of the liquid oil (C) include triglycerides, such as glyceryl trioctanoate, avocado oil, olive oil, sesame oil, rice-bran oil, safflower oil, soybean oil, corn oil, rapeseed oil, sunflower oil, cottonseed oil, mink oil, glyceryl tri-2-ethylhexanoate, and caprylic/capric triglyceride; and fatty acids, such as oleic acid and isostearic acid.

(Content of Each Component in Surfactant Composition)

From the viewpoint of emulsion stability of the component (C) and high remaining properties, the content of each of the components in the surfactant composition of the present invention is as follows.

The content of the anionic surfactant (A) in the surfactant composition is preferably 0.2% by mass or more, more preferably 0.5% by mass or more, and still more preferably 0.8% by mass or more, and it is preferably 20% by mass or less, more preferably 10% by mass or less, still more preferably 6% by mass or less, and yet still more preferably 2% by mass or less.

The content of the branched-type anionic surfactant (a1), preferably the internal olefin sulfonate (IOS) in the surfactant composition is preferably 0.2% by mass or more, more preferably 0.5% by mass or more, still more preferably 0.7% by mass or more, and yet still more preferably 0.8% by mass or more, and it is preferably 15% by mass or less, more preferably 10% by mass or less, still more preferably 6% by mass or less, and yet still more preferably 2% by mass or less.

The content of the cationic surfactant (B), preferably the branched-type cationic surfactant (b1) in the surfactant composition is preferably 0.2% by mass or more, more preferably 0.8% by mass or more, still more preferably 1% by mass or more, and yet still more preferably 1.2% by mass or more, and it is preferably 20% by mass or less, more preferably 10% by mass or less, still more preferably 5% by mass or less, and yet still more preferably 3% by mass or less.

The molar ratio $R_A$: {(A)/[(A)+(B)]} of the amount of the component (A) to the total amount of the component (A) and the component (B) in the surfactant composition is 0.25 or more and 0.60 or less.

From the viewpoint of emulsion stability of the component (C) and high remaining properties, the molar ratio $R_A$ is preferably 0.30 or more, more preferably 0.40 or more, and still more preferably 0.45 or more, and it is preferably 0.58 or less, more preferably 0.55 or less, and still more preferably 0.53 or less.

The molar ratio $R_b$: {[(a1)+(b1)]/[(A)+(B)]} in the surfactant composition is 0.6 or more; and as mentioned above, it is preferably 0.7 or more, more preferably 0.8 or more, and still more preferably 0.9 or more, and it is preferably 1.0 or less.

The content of the liquid oil (C) in the surfactant composition is 0.5% by mass or more, preferably 1% by mass or more, more preferably 3% by mass or more, and still more preferably 6% by mass or more, and it is 60% by mass or less, preferably 40% by mass or less, more preferably 20% by mass or less, and still more preferably 10% by mass or less.

A molar ratio {(C)/[(A)+(B)]} of the amount of the liquid oil (C) to the total amount of the component (A) and the component (B) in the surfactant composition is preferably 0.2 or more, more preferably 1 or more, still more preferably 2 or more, and yet still more preferably 2.3 or more, and it is preferably 10 or less, more preferably 8 or less, still more preferably 5 or less, and yet still more preferably 3 or less.

Water exists as a continuous phase, and the content thereof in the surfactant composition is preferably 35% by mass or more, more preferably 45% by mass or more, still more preferably 55% by mass or more, yet still more preferably 65% by mass or more, and even yet still more preferably 75% by mass or more, and it is preferably 95% by mass or less, and more preferably 90% by mass or less.

(Other Components in Surfactant Composition)

In the surfactant composition of the present invention, optional components, such as a surfactant other than that as mentioned above, an oil solution other than the component (C), an inorganic builder, a solubilizing agent, a diluent, a touch improver, a chelating agent, an antioxidant, a moisturizer, a UV absorber, a pH modifier, and a fragrance, can be appropriately added in conformity with an application thereof.

Examples of the surfactant other than that as mentioned above include an ampholytic surfactant and a nonionic surfactant.

Examples of the ampholytic surfactant include betaine-based surfactants, such as an imidazoline-based betaine, an alkyldimethylamino acetate betaine, a fatty acid amidopropyl betaine, and a sulfobetaine; and amine oxide type surfactants, such as an alkyldimethylamine oxide.

Examples of the nonionic surfactant include at least one fatty acid monoalkanolamide, selected from a polyoxyalkylene alkyl ether, a coconut oil fatty acid monoethanolamide, and so on.

In the case of containing a nonionic surfactant, from the viewpoint of making the component (C) highly remain on the solid surface, a mass ratio {(E)/[(A)+(B)]} of the nonionic surfactant (E) to the total amount of the anionic surfactant (A) and the cationic surfactant (B) should be controlled to 2.0 or less, and it is preferably 0.9 or less, more preferably 0.4 or less, and still more preferably 0.2 or less.

Examples of the inorganic builder include alkaline inorganic salts, such as sodium carbonate, potassium carbonate, sodium bicarbonate, crystalline stratiform sodium silicate, sodium silicate, and an amino silicate, e.g., zeolite; and water-soluble inorganic salts, such as a sulfate, a sulfite, a hydrogensulfate, a hydrochloride, and a phosphate. From the viewpoint of making the component (C) highly remain, the content of the inorganic builder in the surfactant composition is preferably less than 20% by mass, more preferably less than 10% by mass, still more preferably less than 5% by mass, yet still more preferably less than 1% by mass, and even yet still more preferably 0% by mass (namely, the inorganic builder is not contained).

<Production of Surfactant Composition>

The surfactant composition of the present invention can be produced by a conventional method. For example, purified water, such as ion-exchanged water, is heated to preferably 50° C. or higher, and more preferably 60° C. or higher, and preferably 90° C. or lower, and more preferably 70° C. or lower, the respective surfactant components are uniformly mixed and allowed to stand for cooling, and the liquid oil (C) is then added. If desired, an optional component or components are added. As the case may be, an acid or a base is added to regulate the pH, whereby the surfactant composition of the present invention can be obtained.

(Form, Etc. of Surfactant Composition)

Although the dosage form of the surfactant composition of the present invention is not particularly restricted, it is preferably in a liquid form.

As for the form of a product containing the surfactant composition of the present invention, there are preferably exemplified those to be used after shampooing of hair within a bathroom, such as a hair rinse, a hair conditioner, a hair treatment, and a hair pack, namely those to be used in such a manner that after applying on the hair, they are applied well smoothly over the hair and then rinsed away; those to be used at the time of rinsing after washing, such as a fabric softener; and those to be used after car washing, such as a car wax. Among these, from the viewpoint of exhibiting the effects of the surfactant composition of the present invention, it is preferably used as a hair conditioner.

The dosage form of a cleansing agent for skin, a cleansing agent for clothing, a cleansing agent for dish, a cleansing agent for housing, or the like, each containing the surfactant composition of the present invention, is not particularly restricted, and it can be appropriately prepared by a conventional method.

[Remaining Method of Liquid Oil (C)]

A remaining method of the liquid oil (C) of the present invention is a method for bringing the surfactant composition of the present invention into contact with the solid surface.

The "solid surface" as referred to herein is not particularly restricted. As for a suitable solid to which the method of the present invention is applicable, though there is exemplified a hair, the method of the present invention is also applicable to in addition to natural fibers and synthetic fibers, hydrophobic solids, such as a glass, a ceramic, a metal, and a synthetic resin.

The contact method is not particularly limited, too, and examples thereof include a method for dipping the solid in an aqueous solution containing the surfactant composition of the present invention, a method for spraying or applying the foregoing aqueous solution onto the solid surface, and a method for cleansing the solid surface with the foregoing aqueous solution.

With respect to the aforementioned embodiments, the present invention further discloses the following surfactant composition, use thereof, cleansing agent, and production method of a surfactant composition.

<1> A surfactant composition containing an anionic surfactant (A), a cationic surfactant (B), a liquid oil (C), and water, wherein
the water constitutes a continuous phase;
the following molar ratio $R_A$ is 0.25 or more and 0.60 or less; and
the following molar ratio $R_b$ is 0.6 or more:
$R_A$: a molar ratio {(A)/[(A)+(B)]} of the amount of the anionic surfactant (A) to the total amount of the anionic surfactant (A) and the cationic surfactant (B)
$R_b$: a molar ratio {[(a1)+(b1)]/[(A)+(B)]} of the total amount of a branched-type anionic surfactant (a1) and a branched-type cationic surfactant (b1) to the total amount of the anionic surfactant (A) and the cationic surfactant (B).

<2> The composition as set forth in <1>, containing either one of the component (a1) and the component (b1).

<3> The composition as set forth in <1> or <2>, containing both the component (a1) and the component (b1).

<4> The composition as set forth in any of <1> to <3>, wherein the component (A) contains at least one selected from a sulfonic acid salt type surfactant and a sulfuric acid ester salt type surfactant.

<5> The composition as set forth in any of <1> to <4>, wherein the component (a1) is represented by the following formula (1):

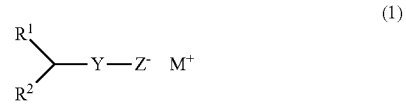

wherein,
$R^1$ and $R^2$ each independently represent a hydrocarbon group which may contain a substituent or a connecting group; the total carbon number of $R^1$ and $R^2$ is 5 or more and 29 or less; Y represents a single bond or a phenylene group; Z represents a group selected from a —$SO_3$ group and a —$OSO_3$ group; and M represents a cation.

<6> The composition as set forth in <5>, wherein $R^1$ and $R^2$ are an aliphatic hydrocarbon group.

<7> The composition as set forth in <5> or <6>, wherein $R^1$ and $R^2$ are an alkyl group, an alkenyl group, or a hydroxyalkyl group.

<8> The composition as set forth in any of <5> to <7>, wherein $R^1$ and $R^2$ may each contain a substituent, such as a hydroxy group, or a connecting group, such as a —COO group.

<9> The composition as set forth in any of <5> to <8>, wherein Y is a single bond.

<10> The composition as set forth in any of <5> to <9>, wherein M is at least one selected from a sodium ion, a potassium ion, a monoethanolammonium ion, a diethanolammonium ion, and a triethanolammonium ion.

<11> The composition as set forth in any of <1> to <10>, wherein the component (a1) is at least one selected from an internal olefin sulfonate (IOS), an alkylbenzenesulfonate, a secondary alkanesulfonate, and a dialkylsulfosuccinate.

<12> The composition as set forth in <11>, wherein the component (a1) is IOS.

<13> The composition as set forth in <11> or <12>, wherein the carbon number of the IOS is 14 or more.

<14> The composition as set forth in any of <11> to <13>, wherein the carbon number of the IOS is 16 or more.

<15> The composition as set forth in any of <11> to <14>, wherein the carbon number of the IOS is 20 or less.

<16> The composition as set forth in any of <11> to <15>, wherein the carbon number of the IOS is 18 or less.

<17> The composition as set forth in any of <11> to <16>, wherein the total content {(16S+18S)/IOS} of an IOS (16S) having 16 carbon atoms and an IOS (18S) having 18 carbon atoms in the IOS is 50% by mass or more.

<18> The composition as set forth in <17>, wherein the {(16S+18S)/IOS} is 70% by mass or more.

<19> The composition as set forth in <17>, wherein the {(16S+18S)/IOS} is 90% by mass or more.

<20> The composition as set forth in <17>, wherein the {(16S+18S)/IOS} is 100% by mass.

<21> The composition as set forth in any of <11> to <20>, wherein the content of an internal olefin sulfonate in which the sulfonate group exists at the 2-position in the IOS (2-position sulfonic acid ratio) is 5% by mass or more.

<22> The composition as set forth in <21>, wherein the 2-position sulfonic acid ratio is 7% by mass or more.

<23> The composition as set forth in <21>, wherein the 2-position sulfonic acid ratio is 10% by mass or more.

<24> The composition as set forth in any of <21> to <23>, wherein the 2-position sulfonic acid ratio is 35% by mass or less.

<25> The composition as set forth in any of <21> to <23>, wherein the 2-position sulfonic acid ratio is 30% by mass or less.

<26> The composition as set forth in any of <21> to <23>, wherein the 2-position sulfonic acid ratio is 28% by mass or less.

<27> The composition as set forth in any of <1> to <26>, wherein the component (B) contains a quaternary ammonium salt type cationic surfactant.

<28> The composition as set forth in any of <1> to <27>, wherein the component (B) contains a branched-type cationic surfactant (b1).

<29> The composition as set forth in any of <1> to <28>, wherein the component (B) is at least one selected from those represented by any of the following formulae (2) and (3):

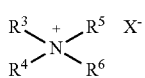

(2)

wherein,
R$^3$ and R$^4$ each independently represent a hydrocarbon group having 6 or more and 26 or less carbon atoms; R$^5$ and R$^6$ each independently represent an alkyl group having 1 or more and 3 or less carbon atoms; and X represents an anion, and

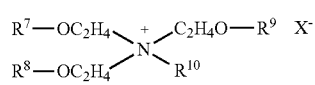

(3)

wherein,
R$^7$, R$^8$, and R$^9$ each independently represent an acyl group having 8 or more and 22 or less carbon atoms or a hydrogen atom, provided that R$^7$, R$^8$, and R$^9$ are not a hydrogen atom at the same time; R$^{10}$ represents an alkyl group having 1 or more and 3 or less carbon atoms; and X represents an anion.

<30> The composition as set forth in any of <1> to <29>, wherein the component (b1) contains at least one selected from those represented by any of the formulae (2) and (3).

<31> The composition as set forth in <29> or <30>, wherein R$^3$ is an aliphatic hydrocarbon group.

<32> The composition as set forth in any of <29> to <31>, wherein R$^3$ is an alkyl group.

<33> The composition as set forth in any of <29> to <32>, wherein R$^4$ is an aliphatic hydrocarbon group or an aryl group.

<34> The composition as set forth in any of <29> to <33>, wherein R$^4$ is an alkyl group or a benzyl group.

<35> The composition as set forth in any of <29> to <34>, wherein the carbon number of the aliphatic hydrocarbon group represented by R$^3$ and R$^4$ is 8 or more.

<36> The composition as set forth in <35>, wherein the carbon number of R$^3$ and R$^4$ is 10 or more.

<37> The composition as set forth in <35>, wherein the carbon number of R$^3$ and R$^4$ is 12 or more.

<38> The composition as set forth in any of <35> to <37>, wherein the carbon number of R$^3$ and R$^4$ is 22 or less.

<39> The composition as set forth in any of <35> to <37>, wherein the carbon number of R$^3$ and R$^4$ is 20 or less.

<40> The composition as set forth in any of <29> to <39>, wherein R$^4$ is a benzyl group.

<41> The composition as set forth in any of <29> to <40>, wherein R$^5$ and R$^6$ are a methyl group.

<42> The composition as set forth in any of <29> to <41>, wherein X$^-$ in the formula (2) is a chlorine ion, a bromine ion, a methyl sulfate ion, or an ethyl sulfate ion.

<43> The composition as set forth in <42>, wherein X$^-$ is a chlorine ion or a methyl sulfate ion.

<44> The composition as set forth in any of <29> to <43>, wherein two of R$^7$, R$^8$, and R$^9$ are an acyl group.

<45> The composition as set forth in any of <29> to <44>, wherein the quaternary ammonium salt represented by the general formula (3) contains at least one selected from a compound in which R$^7$ is an acyl group, and R$^8$ and R$^9$ are a hydrogen atom; a compound in which R$^7$ and R$^8$ are an acyl group, and R$^9$ is a hydrogen atom; and a compound in which R$^7$, R$^8$, and R$^9$ are an acyl group.

<46> The composition as set forth in any of <29> to <45>, wherein the carbon number of the acyl group represented by R$^7$ to R$^9$ is 10 or more.

<47> The composition as set forth in <46>, wherein the carbon number of R$^7$ to R$^9$ is 14 or more.

<48> The composition as set forth in <46>, wherein the carbon number of R$^7$ to R$^9$ is 16 or more.

<49> The composition as set forth in any of <46> to <48>, wherein the carbon number of R$^7$ to R$^9$ is 20 or less.

<50> The composition as set forth in any of <46> to <48>, wherein the carbon number of R$^7$ to R$^9$ is 18 or less.

<51> The composition as set forth in any of <29> to <50>, wherein R$^7$ to R$^9$ are an aliphatic acyl group.

<52> The composition as set forth in any of <29> to <51>, wherein R$^7$ to R$^9$ are a linear aliphatic acyl group.

<53> The composition as set forth in any of <29> to <52>, wherein R$^7$ to R$^9$ are a linear alkanoyl group or a linear alkenoyl group.

<54> The composition as set forth in <53>, wherein the linear alkanoyl group is a hexadecanoyl group or an octadecanoyl group.

<55> The composition as set forth in <53>, wherein the linear alkenoyl group is an oleoyl group.

<56> The composition as set forth in any of <29> to <55>, wherein R$^{10}$ is a methyl group or an ethyl group.

<57> The composition as set forth in any of <29> to <56>, wherein $R^{10}$ is a methyl group.

<58> The composition as set forth in any of <29> to <57>, wherein $X^-$ in the formula (3) is a chlorine ion, a bromine ion, a methyl sulfate ion, or an ethyl sulfate ion.

<59> The composition as set forth in <58>, wherein the $X^-$ is a chlorine ion or a methyl sulfate ion.

<60> The composition as set forth in any of <1> to <59>, wherein the component (C) is in a liquid form at 0° C. to 100° C.

<61> The composition as set forth in any of <1> to <60>, wherein the component (C) is in a liquid form at 0° C. to 45° C.

<62> The composition as set forth in any of <1> to <61>, wherein the component (C) is in a liquid form at 25° C.

<63> The composition as set forth in any of <1> to <62>, wherein a solubility of the component (C) in 100 g of water at 20° C. is 1 g or less.

<64> The composition as set forth in any of <1> to <63>, wherein the component (C) is at least one selected from an ester oil, an ether oil, an aliphatic higher alcohol, a hydrocarbon oil, and a silicone oil.

<65> The composition as set forth in any of <1> to <64>, wherein the content of the component (A) is 0.2% by mass or more.

<66> The composition as set forth in any of <1> to <65>, wherein the content of the component (A) is 0.5% by mass or more.

<67> The composition as set forth in any of <1> to <66>, wherein the content of the component (A) is 0.8% by mass or more.

<68> The composition as set forth in any of <1> to <67>, wherein the content of the component (A) is 20% by mass or less.

<69> The composition as set forth in any of <1> to <68>, wherein the content of the component (A) is 10% by mass or less.

<70> The composition as set forth in any of <1> to <69>, wherein the content of the component (A) is 6% by mass or less.

<71> The composition as set forth in any of <1> to <70>, wherein the content of the component (A) is 2% by mass or less.

<72> The composition as set forth in any of <1> to <71>, wherein the content of the component (a1) is 0.2% by mass or more.

<73> The composition as set forth in any of <1> to <72>, wherein the content of the component (a1) is 0.5% by mass or more.

<74> The composition as set forth in any of <1> to <73>, wherein the content of the component (a1) is 0.7% by mass or more.

<75> The composition as set forth in any of <1> to <74>, wherein the content of the component (a1) is 0.8% by mass or more.

<76> The composition as set forth in any of <1> to <75>, wherein the content of the component (a1) is 15% by mass or less.

<77> The composition as set forth in any of <1> to <76>, wherein the content of the component (a1) is 10% by mass or less.

<78> The composition as set forth in any of <1> to <77>, wherein the content of the component (a1) is 6% by mass or less.

<79> The composition as set forth in any of <1> to <78>, wherein the content of the component (a1) is 2% by mass or less.

<80> The composition as set forth in any of <1> to <79>, wherein the content of the IOS is 0.2% by mass or more.

<81> The composition as set forth in any of <1> to <80>, wherein the content of the IOS is 0.5% by mass or more.

<82> The composition as set forth in any of <1> to <81>, wherein the content of the IOS is 0.7% by mass or more.

<83> The composition as set forth in any of <1> to <82>, wherein the content of the IOS is 0.8% by mass or more.

<84> The composition as set forth in any of <1> to <83>, wherein the content of the IOS is 15% by mass or less.

<85> The composition as set forth in any of <1> to <84>, wherein the content of the IOS is 10% by mass or less.

<86> The composition as set forth in any of <1> to <85>, wherein the content of the IOS is 6% by mass or less.

<87> The composition as set forth in any of <1> to <86>, wherein the content of the IOS is 2% by mass or less.

<88> The composition as set forth in any of <1> to <87>, wherein the content of the component (B) is 0.2% by mass or more.

<89> The composition as set forth in any of <1> to <88>, wherein the content of the component (B) is 0.8% by mass or more.

<90> The composition as set forth in any of <1> to <89>, wherein the content of the component (B) is 1% by mass or more.

<91> The composition as set forth in any of <1> to <90>, wherein the content of the component (B) is 1.2% by mass or more.

<92> The composition as set forth in any of <1> to <91>, wherein the content of the component (B) is 20% by mass or less.

<93> The composition as set forth in any of <1> to <92>, wherein the content of the component (B) is 10% by mass or less.

<94> The composition as set forth in any of <1> to <93>, wherein the content of the component (B) is 5% by mass or less.

<95> The composition as set forth in any of <1> to <94>, wherein the content of the component (B) is 3% by mass or less.

<96> The composition as set forth in any of <1> to <95>, wherein the content of the component (b1) is 0.2% by mass or more.

<97> The composition as set forth in any of <1> to <96>, wherein the content of the component (b1) is 0.8% by mass or more.

<98> The composition as set forth in any of <1> to <97>, wherein the content of the component (b1) is 1% by mass or more.

<99> The composition as set forth in any of <1> to <98>, wherein the content of the component (b1) is 1.2% by mass or more.

<100> The composition as set forth in any of <1> to <99>, wherein the content of the component (b1) is 20% by mass or less.

<101> The composition as set forth in any of <1> to <100>, wherein the content of the component (b1) is 10% by mass or less.

<102> The composition as set forth in any of <1> to <101>, wherein the content of the component (b1) is 5% by mass or less.
<103> The composition as set forth in any of <1> to <102>, wherein the content of the component (b1) is 3% by mass or less.
<104> The composition as set forth in any of <1> to <103>, wherein $R_A$ is 0.30 or more.
<105> The composition as set forth in any of <1> to <104>, wherein $R_A$ is 0.40 or more.
<106> The composition as set forth in any of <1> to <105>, wherein $R_A$ is 0.45 or more.
<107> The composition as set forth in any of <1> to <106>, wherein $R_A$ is 0.58 or less.
<108> The composition as set forth in any of <1> to <107>, wherein $R_A$ is 0.55 or less.
<109> The composition as set forth in any of <1> to <108>, wherein $R_A$ is 0.53 or less.
<110> The composition as set forth in any of <1> to <109>, wherein $R_b$ is 0.7 or more.
<111> The composition as set forth in any of <1> to <110>, wherein $R_b$ is 0.8 or more.
<112> The composition as set forth in any of <1> to <111>, wherein $R_b$ is 0.9 or more.
<113> The composition as set forth in any of <1> to <112>, wherein $R_b$ is 1.0 or less.
<114> The composition as set forth in any of <1> to <113>, wherein the content of the component (C) is 0.5% by mass or more.
<115> The composition as set forth in any of <1> to <114>, wherein the content of the component (C) is 1% by mass or more.
<116> The composition as set forth in any of <1> to <115>, wherein the content of the component (C) is 3% by mass or more.
<117> The composition as set forth in any of <1> to <116>, wherein the content of the component (C) is 6% by mass or more.
<118> The composition as set forth in any of <1> to <117>, wherein the content of the component (C) is 60% by mass or less.
<119> The composition as set forth in any of <1> to <118>, wherein the content of the component (C) is 40% by mass or less.
<120> The composition as set forth in any of <1> to <119>, wherein the content of the component (C) is 20% by mass or less.
<121> The composition as set forth in any of <1> to <120>, wherein the content of the component (C) is 10% by mass or less.
<122> The composition as set forth in any of <1> to <121>, wherein the mass ratio $\{(C)/[(A)+(B)]\}$ is 0.2 or more.
<123> The composition as set forth in any of <1> to <122>, wherein the mass ratio $\{(C)/[(A)+(B)]\}$ is 1 or more.
<124> The composition as set forth in any of <1> to <123>, wherein the mass ratio $\{(C)/[(A)+(B)]\}$ is 2 or more.
<125> The composition as set forth in any of <1> to <124>, wherein the mass ratio $\{(C)/[(A)+(B)]\}$ is 2.3 or more.
<126> The composition as set forth in any of <1> to <125>, wherein the mass ratio $\{(C)/[(A)+(B)]\}$ is 10 or less.
<127> The composition as set forth in any of <1> to <126>, wherein the mass ratio $\{(C)/[(A)+(B)]\}$ is 8 or less.
<128> The composition as set forth in any of <1> to <127>, wherein the mass ratio $\{(C)/[(A)+(B)]\}$ is 5 or less.
<129> The composition as set forth in any of <1> to <128>, wherein the mass ratio $\{(C)/[(A)+(B)]\}$ is 3 or less.
<130> The surfactant composition as set forth in any of <1> to <129>, wherein the content of water is 35% by mass or more.
<131> The composition as set forth in any of <1> to <130>, wherein the content of water is 45% by mass or more.
<132> The composition as set forth in any of <1> to <131>, wherein the content of water is 55% by mass or more.
<133> The composition as set forth in any of <1> to <132>, wherein the content of water is 65% by mass or more.
<134> The composition as set forth in any of <1> to <133>, wherein the content of water is 75% by mass or more.
<135> The composition as set forth in any of <1> to <134>, wherein the content of water is 95% by mass or less.
<136> The composition as set forth in any of <1> to <135>, wherein the content of water is 90% by mass or less.
<137> The composition as set forth in any of <1> to <136>, which is in a liquid form.
<138> The composition as set forth in any of <1> to <137>, further containing a nonionic surfactant (E), wherein a mass ratio $\{(E)/[(A)+(B)]\}$ is 2.0 or less.
<139> The composition as set forth in <138>, wherein the $\{(E)/[(A)+(B)]\}$ is 0.9 or less.
<140> The composition as set forth in <138>, wherein the $\{(E)/[(A)+(B)]\}$ is 0.4 or less.
<141> The composition as set forth in <138>, wherein the $\{(E)/[(A)+(B)]\}$ is 0.2 or less.
<142> The composition as set forth in any of <138> to <141>, wherein the component (E) is at least one selected from a polyoxyalkylene alkyl ether and a coconut oil fatty acid monoalkanolamide.
<143> The composition as set forth in any of <1> to <142>, which is used in order to make the liquid oil (C) remain on the solid surface.
<144> Use of the composition as set forth in any of <1> to <143>, for a hair rinse, a hair conditioner, a hair treatment, a hair pack, a fibrous softener, or a car wax.
<145> A cleansing agent for skin, a cleansing agent for clothing, a cleansing agent for dish, or a cleansing agent for housing, each containing the composition as set forth in any of <1> to <143>.
<146> A method for producing a surfactant composition, including mixing water, a surfactant, and the component (C).
<147> A remaining method of the liquid oil (C), including bringing the composition as set forth above in any of <1> to <143> into contact with the solid surface.

EXAMPLES (1) Measurement of Kinematic Viscosity of Dimethylpolysiloxane

The kinematic viscosity of the dimethylpolysiloxane was measured at 25° C. by using an Ubbelohde viscometer on the basis of JIS Z8803: "Methods for viscosity measurement of liquid".

(2) Measurement of Branching Fraction of Branched-Type Anionic Surfactant (a1) and Branched-Type Cationic Surfactant (b1)

The $^1$H-NMR measurement or the high performance liquid chromatographic measurement was performed under the following condition, peaks derived from the branched structure and peaks derived from the linear structure were detected, and the branching fraction was calculated.

<$^1$H-NMR Measurement Condition>

Superconducting Fourier transform nuclear magnetic resonance apparatus "400-MR", manufactured by Agilent Technologies, Inc.
Resonance frequency: 400 MHZ
Cumulative number: 8 times
Delay time: 10 seconds
Pulse irradiation angle: 45°<High Performance Liquid Chromatographic (HPLC) Measurement Condition>
High Performance Liquid Chromatography Mass Spectrometer (LCMS-2020, manufactured by Shimadzu Corporation)·
Column: UK-C18 HT, manufactured by Imtakt Corporation, 2×50 mm, 3 μm
Eluent: A 0.05% trifluoroacetic acid solution in hexane/methanol/tetrahydrofuran (85/10/5)
Flow rate: 0.8 mL/min (0 to 10 min)→1.2 mL/min (11 to 55 min)·
Detection: Range 500 pA

Examples 1-1 to 1-7 and Comparative Examples 1-1 to 1-5

Surfactants and liquid oils (C) as shown below were prepared.

In a wide-mouthed standard bottle (PS-No. 6, manufactured by Tokyo Glass Kikai Co., Ltd.), each of surfactant raw materials described in Table 1 and water were added. The contents were heated and mixed in a warm water bath at 70° C. for about one hour, and after allowing to stand for cooling to 25° C., the dimethylpolysiloxane was added. The mixture was stirred and shaken until it was uniformly emulsified and dispersed through visual inspection, thereby obtaining a surfactant composition.

Using the obtained surfactant composition, the remaining amount of the liquid oil (C) onto each substrate or base material was measured and evaluated with the method mentioned below. The results are shown in Table 1.

Examples 2-1 to 2-6, Example 3-1, Comparative Example 3-1, Example 4-1, Comparative Example 4-1, Example 5-1, and Comparative Example 5-1

The same procedures as in Example 1-1 were followed, except that in Example 1-1, the condition was changed to that shown in Tables 2 to 5, respectively. The results are shown in Tables 2 to 5.

<Anionic Surfactant (A)>

(1) A1-1: Sodium Internal Olefin Sulfonate (Branching Fraction: 98 Mol %)
(1-1) The Production was Performed by the Method of Production Example 5 of JP 2015-27977 A.

11.9 kg of an internal olefin having 16 carbon atoms and 3.1 kg of an internal olefin having 18 carbon atoms were mixed to obtain 15.0 kg of an internal olefin having 16/18 carbon atoms (mass ratio: 79.4/20.6). Using a thin film sulfonation reactor, the obtained internal olefin having 16/18 carbon atoms was subjected to a sulfonation reaction by passing a sulfur trioxide gas having a concentration of $SO_3$ of 2.8% by volume therethrough.

The resulting sulfonation product was neutralized and hydrolyzed to obtain a sodium internal olefin sulfonate having 16/18 carbon atoms. In the resulting sodium internal olefin sulfonate, the molecular weight was 347.1, the mass ratio of the H-body to the O-body was 87/13, and the content of the raw material internal olefin was less than 100 ppm (less than the GC detection lower limit).

(1-2) Calculation of Branching Fraction

The amount of the branched sulfonic acid was measured by the method [high performance liquid chromatography/mass spectrometry (HPLC-MS)] as described in paragraph of JP 2018-66102 A. The content of the internal sodium olefin sulfate in which the sulfonate group was existent at the 1-position (corresponding to the linear type) was 2% by mass, namely 2 mol %.

(2) A1-2: Sodium Dodecylbenzenesulfonate (Branching Fraction: 100 Mol %)
(2-1) Trade Name: NEOPELEX G-15, Manufactured by Kao Corporation, Active Ingredient: 16% by Mass, Molecular Weight: 348.5
(2-2) Calculation of Branching Fraction According to the $^1$H-NMR measurement, an area ratio of a peak (0.8 ppm) derived from a proton of the terminal methyl group (6H) of each of $R^1$ and $R^2$ of the formula (1) and a peak (2.6 ppm) derived from a proton of the methine group (1H) connecting $R^1$ and $R^2$ to each other was calculated and found to be 6/1. Accordingly, these peaks are derived from the branched structure. In addition, a peak derived from the linear structure (for example, a peak derived from the methylene group adjacent to $R^1$ produced in the case where $R^2$ is a hydrogen atom) was not detected. Accordingly, the branching fraction was defined as 100 mol %.

(3) A1-3: Sodium Dialkylsulfosuccinate (Branching Fraction: 100 Mol %)
(3-1) Trade Name: Aerosol OT, Manufactured by FUJIFILM Wako Pure Chemical Corporation, Main Ingredient: Sodium Di-2-Ethylhexylsuccinate, Active Ingredient: 75% by Mass, Molecular Weight: 444.6
(3-2) Calculation of Branching Fraction According to the $^1$H-NMR measurement, an area ratio of a peak (0.8 ppm) derived from a proton of the terminal methyl group (12H) of each of $R^1$ and $R^2$ of the formula (1) and a peak (4.3 ppm) derived from a proton of the methine group (1H) connecting $R^1$ and $R^2$ to each other was calculated and found to be 12/1. Accordingly, these peaks are derived from the branched structure. In addition, a peak derived from the linear structure was not detected. Accordingly, the branching fraction was defined as 100 mol %.

(4) A1-4: Sodium Secondary Alkane Sulfonate (Branching Fraction: 86 Mol %)
(4-1) Trade Name: LATEMUL PS, Manufactured by Kao Corporation, Active Ingredient: 40% by Mass, Molecular Weight: 314.5
(4-2) Calculation of Branching Fraction According to the $^1$H-NMR measurement, an area ratio of a peak (0.9 ppm) derived from a proton of the terminal methyl group of each of $R^1$ and $R^2$ of the formula (1) and a peak (2.6 to 2.8 ppm) derived from a proton of the methine group or methylene group connecting $R^1$ and $R^2$ to each other was calculated, but it did not become 6/1. An area ratio of a peak (2.6 ppm) derived from a proton of the methine group (1H) connecting $R^1$ and $R^2$ to each other and a peak (2.8 ppm) derived from the methylene group (2H) adjacent to $R^1$ of the linear structure ($R^2$=H) was found to be 73/27.

In consequence, a molar ratio of the branched type to the linear type was 86/14, and the branching fraction was defined as 86 mol %.

(5) A51: Sodium Dodecyl Sulfate (Branching Fraction: 0 Mol %)

Trade name: EMAL 0, manufactured by Kao Corporation, active ingredient: 99% by mass, molecular weight: 288.4

<Cationic Surfactant (B)>

(1) b1-1: Dialkyl(C12 to 18) Dimethylammonium Chloride (branching fraction: 100 mol %)

(1-1) Trade name: QUARTAMIN D-2345P, manufactured by Kao Corporation, which is the compound of the formula (2), active ingredient: 75% by mass, molecular weight: 474.3

(1-2) According to the $^1$H-NMR measurement, an area ratio of a peak (1.7 ppm) derived from a proton of the methylene group (4H) second adjacent to nitrogen in each of $R^3$ and $R^4$ of the formula (2) and a peak (3.1 ppm) derived from a proton of the methyl group (6H) of each of $R^5$ and $R^6$ was calculated and found to be 4/6. Accordingly, these peaks are derived from the branched structure. In addition, a peak derived from the linear structure was not detected. Accordingly, the branching fraction was defined as 100 mol %.

(2) b1-2: Quaternary Ammonium Salt Represented by General Formula (3) (Branching Fraction: 63 Mol %)

(2-1) b1-2 was produced by the following method.

A one-liter reactor was charged with triethanolamine (1.0 mol, "Triethanolamine-S", manufactured by Nippon Shokubai Co., Ltd.), a semi-cured palm oil fatty acid (1.65 mols, "Palmac 605T", manufactured by Acidchem International Sdn. Bhd.), and 0.28 g of BHT and then purged with nitrogen. Subsequently, the pressure was reduced from atmospheric pressure to 13.3 kPa at 170° C. over one hour while bubbling nitrogen, and an esterification reaction was performed for 7 hours, thereby obtaining 569 g of a triethanolamine ester having an acid value of 2.0 mg KOH/g.

512 g (0.9 mols) of the obtained triethanolamine ester and 0.7 g of BHT were mixed, and 107.8 g (0.855 mols) of dimethyl sulfate was added dropwise in a nitrogen atmosphere at atmospheric pressure and at 45 to 65° C. over 2 hours. The contents were aged at 60 to 65° C. for 1.5 hours, and 84.9 g of ethanol was added and mixed at 55 to 65° C. for 0.5 hours such that the amount of the solvent in the final quaternary ammonium salt became 12% by mass, thereby obtaining a quaternary ammonium salt.

The obtained quaternary ammonium salt was analyzed by means of high performance liquid chromatography (HPLC) and quantitatively determined using tetraoctylammonium bromide as an internal standard substance. As a result, the reaction product contained 88% by mass of the quaternary ammonium salt represented by the general formula (3) and 12% by mass of ethanol. The molecular weight was 716.2.

(2-2) Calculation of Branching Fraction

The analysis with a high performance liquid chromatograph was performed. As a result, the reaction product was found to be a mixture of a monoester body (5 min), a diester body (10 min), and a triester body (23 min). A molar ratio of these ester bodies was 37/52/11. The diester body and the triester body are corresponding to the branched type, and therefore, the branching fraction becomes 63 mol %.

(3) b1-3: Benzalkonium Salt Type Quaternary Ammonium Salt (Branching Fraction: 100 Mol %)

(3-1) Trade Name: SANIZOL C, Manufactured by Kao Corporation, Active Ingredient: 50% by Mass, Molecular Weight: 368.1

(3-2) Calculation of Branching Fraction

According to the $^1$H-NMR measurement, an area ratio of a peak (1.9 ppm) derived from a proton of the methylene group (2H) second adjacent to nitrogen in $R^3$ of the formula (2), a peak (4.5 ppm) derived from a proton of the benzyl group adjacent to nitrogen in $R^4$, and a peak (3.0 ppm) derived from a proton of the methyl group (6H) of each of $R^5$ and $R^6$ was calculated and found to be 2/2/6. Accordingly, these peaks are derived from the branched structure. In addition, a peak derived from the linear structure was not detected. Accordingly, the branching fraction was defined as 100 mol %.

<Liquid Oil (C)>

EXCEPARL IPM: Isopropyl myristate, manufactured by Kao Corporation, active ingredient: 100% by mass.

KF-96L-50cs: Silicone oil, manufactured by Shin-Etsu Chemical Co., Ltd., kinematic viscosity: 50 mm$^2$/s (at 25° C.), active ingredient: 100% by mass <Ampholytic Surfactant>

AMPHITOL 20AB: Lauramidopropyl betaine, manufactured by Kao Corporation, active ingredient: 30% by mass <Quantitative Determination of Remaining Amount of Surfactant Composition onto Each Substrate or Base Material>

[Quantitative Determination 1 of Liquid Oil (Isopropyl Myristate)]

100 mg of each composition was applied onto the substrate and rinsed with 10 mL of tap water. Thereafter, the resultant was dipped in 20 mL of CHCl$_3$, and the liquid oil (isopropyl myristate) remaining on the substrate was extracted by applying ultrasonic waves over 30 minutes. The resulting extract was diluted with methanol to prepare a solution for measurement, which was then subjected to quantitative determination for the remaining amount of the liquid oil by using a high-performance liquid chromatography mass spectrometer (LCMS-2020, manufactured by Shimadzu Corporation) under the following measurement condition.

(Measurement Condition).

Column: UK-C18 HT, manufactured by Imtakt Corporation, 2×50 mm, 3 μm

Eluent:
A: 10 mM CH$_3$COONH$_4$ solution in water
B: 10 mM CH$_3$COONH$_4$ solution in methanol
C: 10 mM CH$_3$COONH$_4$ solution in ethanol Flow rate: 0.6 mL/min Method: A 40%, B 30%, and C 30% (0 min)—A 0%, B 50%, and C 50% (15 to 20 min)·

Detection: ESI mode positive m/z=288.3

[Quantitative Determination 2 of Liquid Oil (Silicone)]

100 mg of each surfactant composition was uniformly applied onto the surface of the following substrate or base material and rinsed with 10 mL of tap water, and then, deuterated chloroform (CDCl$_3$) was put thereinto until the substrate or base material was completely dipped therein (2 mL in the case of the glass substrate and the polypropylene substrate, and 10 mL in the case of the stainless steel substrate and the cotton or hair base material).

The liquid oil (silicone) remaining on the substrate or base material was extracted by applying ultrasonic waves over 30 minutes, pyrazine as an internal standard was added to the extract, and the mixture was subjected to the $^1$H-NMR measurement with a superconducting Fourier transform nuclear magnetic resonance apparatus "400-MR", manufactured by Agilent Technologies, Inc.

The remaining amount of the silicone was calculated from the integrated ratio of peak areas of pyrazine (8.6 ppm) and silicone (0.0 ppm).

(Substrate or Base Material)

Polypropylene (PP) substrate: manufactured by Nippon Testpanel Co., Ltd., 1×17×25 mm Glass substrate: manufactured by Matsunami Glass Ind., Ltd., 1×17×25 mm Stainless steel substrate: manufactured by Standard Test Piece Inc., 1×20×50 mm Cotton base material: 1×60×60 mm Hair base material: manufactured by Beaulax Co., Ltd., 1 g

TABLE 1

| | | Blending formulation of surfactant composition [% by mass] | | | | | Molar ratio | | Evaluation results Remaining amount of |
|---|---|---|---|---|---|---|---|---|---|
| | | Anionic surfactant (A) | | Cationic surfactant (B) | Liquid oil (C) EXCEPARL | | $R_A$ [(A)/ (A) + (B)] | $R_b$ [(a1) + (b1)/ (A) + (B)] | (C) onto PP substrate |
| | | a1-1 | a51 | b1-1 | IPM | Water | | | [mg] |
| Example | 1-1 | 1.3 | 0.0 | 1.8 | 8.0 | Remainder | 0.50 | 1.0 | 1.05 |
| | 1-2 | 0.8 | 0.5 | 1.9 | 8.0 | Remainder | 0.50 | 0.8 | 0.58 |
| | 1-3 | 0.3 | 0.9 | 1.9 | 8.0 | Remainder | 0.50 | 0.6 | 0.22 |
| | 1-4 | 0.0 | 0.9 | 2.5 | 8.0 | Remainder | 0.40 | 0.6 | 0.24 |
| | 1-5 | 0.8 | 0.0 | 2.4 | 8.0 | Remainder | 0.30 | 1.0 | 0.39 |
| | 1-6 | 1.0 | 0.0 | 2.1 | 8.0 | Remainder | 0.40 | 1.0 | 1.00 |
| | 1-7 | 1.6 | 0.0 | 1.5 | 8.0 | Remainder | 0.60 | 1.0 | 0.64 |
| Comparative Example | 1-1 | 1.5 | 0.5 | 1.2 | 8.0 | Remainder | 0.70 | 0.8 | 0.12 |
| | 1-2 | 2.1 | 0.2 | 0.8 | 8.0 | Remainder | 0.80 | 0.9 | N.D. |
| | 1-3 | 2.0 | 0.0 | 1.2 | 8.0 | Remainder | 0.70 | 1.0 | 0.15 |
| | 1-4 | 0.5 | 0.0 | 2.7 | 8.0 | Remainder | 0.20 | 1.0 | 0.18 |
| | 1-5 | 0.0 | 0.0 | 1.1 | 8.0 | Remainder | 0.00 | 1.0 | 0.06 |

*: The branching fraction of a1-1 is 98 mol %

The branching fraction of a51 is 0 mol %.

The branching fraction of b1-1 is 100 mol %.

TABLE 2

| | | Blending formulation of surfactant composition [% by mass] | | | | | | | Molar ratio | | Evaluation results Remaining amount of (C) onto PP substrate [mg] |
|---|---|---|---|---|---|---|---|---|---|---|---|
| | | Anionic surfactant (A) | | Cationic surfactant (B) | | Liquid oil (C) | | | $R_A$ [(A)/ (A) + (B)] | $R_b$ [(a1) + (b1)/ (A) + (B)]} | |
| | | Kind (branching fraction) | Amount | Kind (branching fraction) | Amount | Kind | Amount | Water | | | |
| Example | 2-1 | a1-1 (98 mol %) | 1.3 | b1-1 (100 mol %) | 1.8 | EXCEPARL IPM | 8.0 | Remainder | 0.50 | 1.0 | 1.05 |
| | 2-2 | a1-2 (100 mol %) | 1.3 | b1-1 (100 mol %) | 1.8 | EXCEPARL IPM | 8.0 | Remainder | 0.50 | 1.0 | 0.89 |
| | 2-3 | a1-3 (100 mol %) | 1.7 | b1-1 (100 mol %) | 1.8 | EXCEPARL IPM | 8.0 | Remainder | 0.50 | 1.0 | 0.77 |
| | 2-4 | a1-4 (86 mol %) | 1.2 | b1-1 (100 mol %) | 1.8 | EXCEPARL IPM | 8.0 | Remainder | 0.50 | 0.9 | 0.93 |
| | 2-5 | a1-1 (98 mol %) | 1.3 | b1-2 (63 mol %) | 2.7 | EXCEPARL IPM | 8.0 | Remainder | 0.50 | 0.8 | 0.84 |
| | 2-6 | a1-1 (98 mol %) | 1.3 | b1-3 (100 mol %) | 1.4 | EXCEPARL IPM | 8.0 | Remainder | 0.50 | 1.0 | 0.87 |

TABLE 3

| | Blending formulation of surfactant composition [% by mass] | | | | Molar ratio | | Remaining amount of (C) |
|---|---|---|---|---|---|---|---|
| | Anionic surfactant (A) a1-1 | Cationic surfactant (B) b1-1 | Liquid oil (C) KF-96L-50cs | Water | $R_A$ [(A)/ (A) + (B)] | $R_b$ [(a1) + (b1)/ (A) + (B)]} | onto PP substrate [mg] |
| Example 3-1 | 2.6 | 3.7 | 8.0 | Reminder | 0.50 | 1.0 | 1.74 |
| Comparative Example 3-1 | 0 | 2.1 | 8.0 | Reminder | 0.00 | 1.0 | 0.43 |

*: The branching fraction of a1-1 is 98 mol %
The branching fraction of b1-1 is 100 mol %.

TABLE 4

| | Blending formulation of surfactant composition [% by mass] | | | | Molar ratio | | Remaining amount of (C) onto substrate or base material [mg] | | |
|---|---|---|---|---|---|---|---|---|---|
| | Anionic surfactant (A) a1-1 | Cationic surfactant (B) b1-1 | Liquid oil (C) EXCEPARL IPM | Water | $R_A$ [(A)/ (A) + (B)] | $R_b$ [(a1) + (b1)/ (A) + (B)] | PP substrate | Glass substrate | Stainless steel substrate |
| Example 4-1 | 1.3 | 1.8 | 8.0 | Remainder | 0.50 | 1.0 | 1.05 | 0.81 | 0.66 |
| Comparative Example 4-1 | 0 | 1.1 | 8.0 | Remainder | 0.00 | 1.0 | 0.06 | 0.29 | 0.1 |

*: The branching fraction of a1-1 is 98 mol %
The branching fraction of b1-1 is 100 mol %.

TABLE 5

| | Blending formulation of surfactant composition [% by mass] | | | | | Molar ratio | | Remaining amount of (C) onto base material [mg] | |
|---|---|---|---|---|---|---|---|---|---|
| | Anionic surfactant (A) a1-1 | Cationic surfactant (B) b1-1 | Ampholytic surfactant AMPHITOL 20AB | Liquid oil (C) EXCEPARL IPM | Water | $R_A$ [(A)/ (A) + (B)] | $R_b$ [(a1) + (b1)/ (A) + (B)] | Cotton base material | Hair base material |
| Example 5-1 | 0.8 | 1.1 | 1.4 | 8.0 | Remainder | 0.50 | 1.0 | 5.25 | 1.97 |
| Comparative Example 5-1 | 0 | 1.1 | 0 | 8.0 | Remainder | 0.00 | 1.0 | 4.09 | 1.44 |

*: The branching fraction of a1-1 is 98 mol %
The branching fraction of b1-1 is 100 mol %.

From Tables 1 to 5, it is noted that the surfactant compositions of the Examples are able to make the liquid oil highly remain on the solid surface to be washed, as compared with the surfactant compositions of the Comparative Examples.

INDUSTRIAL APPLICABILITY

The surfactant composition of the present invention is useful as a surfactant composition capable of making the liquid oil highly remain on the solid surface.

The invention claimed is:

1. A surfactant composition, comprising:
0.2% by mass to 2.6% by mass of an anionic surfactant (A);
0.2% by mass to 3.7% by mass of a cationic surfactant (B);
a liquid oil (C) and
water,
wherein:
the water constitutes a continuous phase;
the following molar ratio $R_A$ is 0.40 or more and 0.60 or less:
$R_A$: a molar ratio $\{(A)/[(A)+(B)]\}$ of an amount of the anionic surfactant (A) to a total amount of the anionic surfactant (A) and the cationic surfactant (B);
the following molar ratio $R_b$ is 0.7 or more:
$R_b$: a molar ratio $\{[(a1)+(b1)]/[(A)+(B)]\}$ of a total amount of a branched anionic surfactant (a1) and a branched cationic surfactant (b1) to the total amount of the anionic surfactant (A) and the cationic surfactant (B);
the branched anionic surfactant (a1) is represented by the following formula (1):

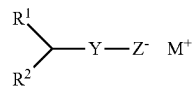
(1)

wherein:
$R^1$ and $R^2$ each independently represent a hydrocarbon group which may comprise a substituent or a connecting group; the total carbon number of $R^1$ and $R^2$ is 5 or more and 29 or less;
Y represents a single bond or a phenylene group;
Z represents a group selected from a —$SO_3$ group and a —$OSO_3$ group; and
M represents a cation; and
the cationic surfactant (B) is at least one quaternary ammonium salt cationic surfactant selected from those represented by any of the following general formulae (2) and (3):

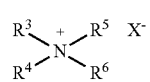
(2)

wherein:
$R^3$ and $R^4$ each independently represent a hydrocarbon group having 6 or more and 26 or less carbon atoms;
$R^5$ and $R^6$ each independently represent an alkyl group having 1 or more and 3 or less carbon atoms; and
$X^-$ represents an anion,
and

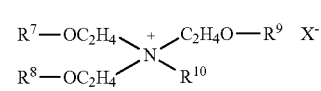
(3)

wherein:
$R^7$, $R^8$, and $R^9$ each independently represent an acyl group having 8 or more and 22 or less carbon atoms or a hydrogen atom, provided that $R^7$, $R^8$, and $R^9$ are not a hydrogen atom at the same time;
$R^{10}$ represents an alkyl group having 1 or more and 3 or less carbon atoms; and
$X^-$ represents an anion.

2. The surfactant composition according to claim 1, wherein the anionic surfactant (A) is at least one selected from a sulfonic acid salt surfactant and a sulfuric acid ester salt surfactant.

3. The surfactant composition according to claim 1, wherein the branched anionic surfactant (a1) is an internal olefin sulfonate.

4. The surfactant composition according to claim 3, wherein the carbon number of the internal olefin sulfonate is 14 or more and 22 or less.

5. The surfactant composition according to claim 1, wherein the amount of the anionic surfactant (A) is 0.2% by mass or more and 2% by mass or less.

6. The surfactant composition according to claim 1, wherein an amount of the cationic surfactant (B) is 0.2% by mass or more and 3% by mass or less.

7. The surfactant composition according to claim 1, wherein an amount of the liquid oil (C) is 0.5% by mass or more and 60% by mass or less.

8. The surfactant composition according to claim 1, wherein a mass ratio $\{(C)/[(A)+(B)]\}$ of the amount of the liquid oil (C) to the total amount of the anionic surfactant (A) and the cationic surfactant (B) is 0.2 or more and 10 or less.

9. The surfactant composition according to claim 1, wherein an amount of water is 35% by mass or more.

10. The surfactant composition according to claim 1, wherein an amount of water is 45% by mass or more and 95% by mass or less.

11. The surfactant composition according to claim 1, which is employed in order to make the liquid oil (C) remain on a solid surface.

12. A method, comprising:
contacting the surfactant composition according to claim 1 with a solid surface such that the liquid oil (C) remains on the solid surface.

* * * * *